US007575874B2

(12) United States Patent
van Dongen

(10) Patent No.: US 7,575,874 B2
(45) Date of Patent: Aug. 18, 2009

(54) METHOD AND PROBES FOR THE DETECTION OF A TUMOR SPECIFIC FUSION PROTEIN

(75) Inventor: Jacobus Johannes Maria van Dongen, Nieuwerkerk aan den IJssel (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 203 days.

(21) Appl. No.: 11/122,775

(22) Filed: May 5, 2005

(65) Prior Publication Data

US 2005/0260684 A1 Nov. 24, 2005

Related U.S. Application Data

(63) Continuation of application No. PCT/NL03/000776, filed on Nov. 6, 2003.

(30) Foreign Application Priority Data

Nov. 7, 2002 (EP) .................... 02079666

(51) Int. Cl.
*G01N 33/533* (2006.01)
(52) U.S. Cl. .............. 435/7.1; 435/7.5; 435/7.91; 435/7.92; 435/69.7; 436/501
(58) Field of Classification Search ............. 435/7.1, 435/7.5, 7.91, 7.92, 69.7; 436/501
See application file for complete search history.

(56) References Cited

FOREIGN PATENT DOCUMENTS

| | | |
|---|---|---|
| EP | 1 382 965 A1 | 1/2004 |
| WO | WO 01/75453 A2 | 10/2001 |
| WO | WO 02/088733 A1 | 11/2002 |
| WO | WO 2004/042398 A1 | 5/2004 |

OTHER PUBLICATIONS

Kane et al. (Analytical Biochemistry, vol. 278, 2000, pp. 29-38).*
Emig et al., Accurate and rapid analysis of residual disease in patients with CML using specific fluorescent hybridization probes for real time quantitative RT-PCR, Leukemia, 1999, pp. 1825-1832, vol. 13, No. 11.
Ueda et al., Homogeneous Noncompetitive Immunoassay Based on the Energy Transfer Between Fluorolabeled Antibody Variable Domains (Open Sandwich Fluoroimmunoassay), BioTechniques, Oct. 1999, pp. 738-742, vol. 27.
PCT International Preliminary Examination Report, PCT/NL03/00776, dated Feb. 10, 2005.
PCT Search Report, PCT/NL03/00776, dated Mar. 12, 2004.

* cited by examiner

*Primary Examiner*—Lisa V Cook
(74) *Attorney, Agent, or Firm*—TraskBritt, P.C.

(57) ABSTRACT

This invention relates to the detection of fusion proteins. The invention provides a set of at least a first and a second molecular probe, each probe provided with a dye wherein the dyes together allow energy transfer, at least one probe provided with a reactive group allowing juxtaposing at least the first and second probes wherein the reactive group allows to modulate of juxtaposing the probes such that there is an increased likelihood of energy transfer between the dyes. A method is provided which permits detecting the presence of a fusion protein in a cell at the single cell level.

3 Claims, 4 Drawing Sheets

METHOD AND PROBES FOR THE DETECTION OF A TUMOR SPECIFIC FUSION PROTEIN

CROSS-REFERENCE TO RELATED APPLICATIONS

This application is a continuation of PCT International Patent Application No. PCT/NL2003/000776, filed on Nov. 6, 2003, designating the United States of America, and published, in English, as PCT International Publication No. WO 2004/042398 A1 on May 21, 2004, which application claims priority to European Patent Application No. 02079666.0 filed Nov. 7, 2002, the contents of the entirety of each of which are hereby incorporated herein by this reference.

TECHNICAL FIELD

This invention relates to the detection of, among others, tumor-specific fusion proteins. More specifically, the invention relates to techniques that indicate the presence of chromosomal translocations by detecting the presence of a fusion protein at the single cell level. In the diagnosis of various types of cancer, such as leukemias, lymphomas and solid tumors, chromosome aberrations are frequently used for classification into prognostically relevant subgroups.[1] Many of these chromosome aberrations result in fusion genes, i.e., aberrantly coupled genes coupled via the upstream part of one gene to the downstream part of the other gene, or vice versa. Fusion genes can be transcribed into fusion gene transcripts and translated into fusion proteins. Generally, fusion proteins play an important role in the oncogenetic process. So far, more than a hundred different fusion genes and fusion proteins have been described in various types of cancer.[2-5]

BACKGROUND

The term "cancer" comprises a heterogeneous group of neoplasms, in which each type has its own characteristics when considering its malignant potential and its response to therapy. It goes without saying that accurate diagnosis and classification of the various cancer types is pre-eminent in helping to select the most effective therapy. Furthermore, a diagnostic method allowing the detection of small numbers of malignant cells in a high background of normal cells during therapy is essential for evaluating treatment effectiveness and for anticipating an impending relapse.

Chromosomal translocations can be detected by a wide array of techniques, most of which entail modern biomolecular technology. Cytogenetic techniques include conventional chromosomal banding techniques (karyotyping) and fluorescence in situ hybridization (FISH) which uses fluorescently labeled probes. Polymerase chain reaction-(PCR—) based strategies can be used to detect fusions of chromosomal breakpoints as can be found in chromosomal translocations, inversions and deletions using primers located at each side of the breakpoint. DNA amplification can only be used for chromosome aberrations in which breakpoints cluster in a small area. In most cases, breakpoints spread over large intronic regions, but several translocations, inversions and deletions give rise to fusion genes and fusion transcripts suitable for PCR amplification after a reverse transcription step (RT-PCR).

Most commonly used techniques aimed at detecting specific Chromosomal aberrations involve analysis at the chromosomal or nucleic acid (DNA or RNA) level. An advantage of such genetic fusion markers is their direct involvement in oncogenesis. Accordingly, their presence is constant all over disease evolution. However, a major drawback of fusion markers relates to the fact that variations in the level of gene transcription and/or gene translation during the disease and particularly during therapy cannot be excluded. Thus, variations in expression of a fusion gene transcript or a fusion protein make it difficult to correlate the level of detection of the marker to the amount of malignant cells. This implies that detection of a fusion gene product is preferably performed at the protein level in individual cells.

A fusion protein comprises parts of at least two proteins that correspond to, and were originally transcribed by and translated from the originally separated genes. Fusion proteins are uniquely characterized by a fusion point, where the two proteins meet. Fusion points are often antigenically exposed, comprising distinct epitopes which sometimes can be immunologically detected.

Initially, attempts were made to raise fusion-protein specific antibodies by generating antibodies against a peptide corresponding to the joining region of a fusion protein. This approach has rarely been successful, mainly because of the fact that it is difficult to find immunological reagents that are exclusively reactive with a fusion protein and not with the non-fusion proteins that are normally produced in a cell. If fusion-specific antibodies were obtained, they were generally not applicable to fluorescence microscopy or flow cytometry.[6-8] For example, the ERP-FP1 antibody against the BCR-ABL fusion protein works well in Western blotting procedures but is not successful in microscopic studies on human BCR-ABL positive leukemias.[6,7] Moreover, considering the large variation within individual rearrangements seen in chromosomal translocations and depending on the localization of the breakpoint within the non-aberrant gene (even when the translocations occur within the same two genes) wherein different fusion proteins can be generated, it is deemed likely that within each separate case of fusion proteins, new fusion points arise. Detection of fusion proteins by specific immunologic detection of the fusion-point epitope of the fusion protein has therefore never been widely applicable.

An alternative method for the specific detection of fusion proteins involves the application of a so-called catching antibody which recognizes one part of a fusion protein and a labeled detection antibody which recognizes an other part of a fusion protein. In such a system, a catching antibody is bound to a solid support layer, such as an ELISA plate or a dipstick. A catching antibody may also be immobilized onto beads that can be analyzed by flow cytometry.[9] Following incubation of a catching antibody with a cellular lysate suspected of containing the fusion protein, bound fusion protein is detected by a labeled detection antibody. Although elegant and easy to perform, a catching/detection antibody system cannot be applied practically to detect an intracellular fusion protein without disrupting the cell integrity. Most tumor-specific fusion proteins are localized intracellularly, e.g. nuclear transcription factors, or signaling molecules which reside in the cytoplasm or which shuttle between the cytoplasm and the nucleus. Thus, a catching/detection antibody system does not allow detection of an intracellular fusion protein at the single cell level.

Co-localization of two differentially labeled antibodies against two different parts of a fusion protein could in theory prove the presence of a fusion protein in a single cell. However, full proof of co-localization requires analysis by confocal laser scanning microscopy (CLSM). Even then it is generally not straightforward to evaluate co-localization of two antibodies because the recognized normal proteins, that are derived from the normal genes on the unaffected chromosomes, can cause a background staining which interferes with the detection of the fusion protein. Further, CLSM has the great disadvantage that it requires a specialized and well-equipped laboratory and trained and highly skilled personnel. Such a time-consuming and highly specialized technique is not desirable for routine diagnostic procedures e.g. in a clinical setting.

All of the above indicate that there is a specific need for an improved method to detect a fusion protein, which can preferably be used in a clinical laboratory. Particularly challenging is the detection of an intracellular fusion protein at the single cell level.

SUMMARY OF THE INVENYION

The invention provides the insight that fluorescence resonance energy transfer (FRET) technology can be used to detect the presence of a fusion protein. The invention provides a method for detecting the presence of a fusion protein in a cell using a set of at least a first and a second molecular probe, each probe capable of recognizing a binding site positioned at opposite sides of the fusion region of the fusion protein, each probe provided with a dye wherein the dyes together allow energy transfer, comprising providing a set of probes, providing a sample comprising a cell, contacting the sample with the probes under conditions that allow juxtaposing the probes on the fusion protein, removing any unbound and any non-specifically bound probe and detecting juxtaposition of the probes via FRET to determine the presence of the fusion protein.

Also provided is a set of at least a first and a second molecular probe, each probe provided with a dye wherein the dyes together allow energy transfer; at least one probe provided with a reactive group allowing juxtaposing the at least first and second probe, wherein the reactive group allows to modulate juxtaposing the probes such that there is an increased likelihood of energy transfer between the dyes. According to the invention, a molecular probe is capable of specifically binding to a biological molecule of interest via its so-called binding domain. Following binding of a at least a first and a second probe to a molecule of interest via the binding domain, a reactive group can be used to modulate juxtapositioning. A reactive group has no or a minimal tendency to compete with the binding domain for binding to a molecule of interest. Herewith, a set of probes of the invention is distinguished from known sets of antibody probes that are clustered or juxtaposed by the mere binding to one antigenic molecule or complex. A reactive group preferably remains available for modulating the spatial organization of juxtaposed probes after the probe is bound to a molecule of interest. In one embodiment, the molecule of interest is a protein, preferably a fusion protein, more preferably an oncogenic fusion protein. Particularly preferred is a set of a first and a second molecular probe wherein each probe is capable of recognizing and binding to a binding site (epitope) positioned at opposite sides of the fusion region of the fusion protein. Of course, when using a set of probes wherein each probe binds to a different epitope of a molecule of interest (e.g. epitopes at the C- and N-terminal side of the fusion region of a fusion protein), the different epitopes should not interact with each other in either an inter- or intramolecular fashion because this would obviously interfere with probe binding. Different probes within a set of probes are therefore capable of binding to different, essentially non-interacting epitopes. This is unlike the situation described in WO 01/75453 relating to methods for detecting an entity by virtue of two probes (reporters), wherein the two probes may bind to the same target site on the entity, either substantially simultaneously or sequentially, or to different target sites. The reporters/probes of WO 01/75453 may be used for detecting a chimeric fusion protein. It is mentioned that one reporter preferably binds an SH2 domain and the other reporter binds to an SH2-binding site, i.e. the probes of WO 01/75453 preferably bind to interacting epitopes. Such probes and detection methods are clearly distinct from the present invention because a FRET-based method as provided herein would simply not work when using a set of probes wherein different probes are directed against either identical or interacting epitopes. Moreover, none of the probes of WO 01/75453 is provided with a reactive group allowing juxtaposing the probes.

The present invention provides a diagnostic kit comprising a set of probes according to the invention and a method using a set of probes for detecting the presence of a fusion protein in the diagnosis and/or classification of a disease as well as before, during and after treatment of a disease to evaluate the effectiveness of the treatment.

Also provided is a method for producing a probe set according to the invention comprising contacting each probe with a dye to form a conjugate between the probe and the dye and purifying the conjugate, further comprising contacting at least one probe with a reactive group or a derivative thereof to form a conjugate between the probe and the reactive group and purifying the conjugate.

Fluorescence resonance energy transfer (FRET) is a distance-dependent interaction between the electronic excited states of two dye molecules in which a "donor" molecule, after excitation by a light source, transfers its energy to an"acceptor" molecule. In general, the donor and acceptor dyes are different, in which case FRET can be detected by the appearance of sensitized fluorescence of the acceptor or by quenching of donor fluorescence. When the donor and acceptor dyes are the same, FRET can be detected by the resulting fluorescence depolarization. Energy transfer occurs when the emission spectrum of the acceptor overlap significantly. To achieve resonance energy transfer, the donor must absorb light and transfer it through the resonance of excited electrons to the acceptor.[10-13] FRET is usually based on the interaction between donor and acceptor dyes that are both fluorescent. However, non-fluorescent acceptor dyes can also be used. Nonfluorescent acceptor dyes can be advantageous because they eliminate the background fluorescence that results from direct (i.e., nonsensitized) acceptor excitation. In the present invention, it is possible to monitor juxtaposed probes on a fusion protein using a fluorescent donor dye and a nonfluorescent acceptor dye. Specific binding of a set of probes to the native proteins, e.g. proteins A and B, will give a basal fluorescence signal. Upon close juxtapositioning of a set of probes on a A-B fusion protein, FRET between the probes will quench the donor fluorescence. Rather than measuring an increase in acceptor fluorescence, use of a nonfluorescent acceptor involves measuring a decrease in donor fluorescence. Generally speaking, detection of a decreased signal is less sensitive compared to detection of an increased signal. Therefore, a method according to the invention is preferably practiced using a fluorescent donor and a fluorescent acceptor dye.

For energy transfer to take place, the fluorescence emission wavelength of the donor must be lower than the excitation wavelength of the acceptor; that is, the process must be energetically "downhill". Sufficiently close juxtaposition of the two dyes, generally closer than 100 Angstrom but preferably closer than 50 Angstrom, is essential for energy transfer between the donor/acceptor pair. One Angstrom, a metric unit of length, is equal to 0.1 nanometer or $10^{-10}$ meter. The FRET energy transfer efficiency is inversely proportional to the sixth power of the distance between the donor and the acceptor. The insight is provided that, due this high sensitivity to distance, FRET is especially suitable to detect the juxtaposing of two different dye-conjugated probes on a fusion protein.

In a preferred embodiment of the invention, a probe set comprises a set of at least two dye-conjugated antibodies, each antibody capable of recognizing a binding site positioned at opposite sides of the fusion region of a fusion protein. A suitable antibody comprises a conventional (poly- or monoclonal) or a synthetic antibody or a binding fragment functionally equivalent thereto, such as a Fab', Fab, a single chain Fv fragment, a diabody (a single chain Fv dimer) and the like. For example, a chimeric fusion protein A-B can be detected via FRET using a set of dye-conjugated probes, e.g. an anti-A antibody and an anti-B antibody. In a preferred embodiment, a sample is contacted with two antibodies, one against domain A and the other against domain B of a fusion protein to detect the presence of an A-B fusion protein in a cell sample. One antibody is labeled with a FRET donor dye and an other with a FRET acceptor dye. Only when domain A is in close proximity to domain B, e.g. when both are part of the same protein molecule, the two antibodies become sufficiently close together ("juxtaposed") which allows the donor/acceptor pair to induce a detectable FRET fluorescence signal.

Simultaneous reactivity of more than one different antibodies with the same protein molecule needs recognition of two different binding sites or epitopes that are sufficiently separated in order to prevent steric hindering of the antibodies. For example, simultaneous application of an antibody against the variable (V) domains and an antibody against the constant (C) domains of T-cell receptor (TCR) molecules on the cell surface of a T-lymphocyte gives no reliable and reproducible results. However, simultaneous application of V domain antibodies and an antibody against the CD3 molecule, which is closely associated with the TCR molecule, yielded excellent staining results in both flow cytometry and microscopy.[14] These data suggest that the distance between two epitopes on the same protein should preferably be more than approximately 80 Ångstrom to be recognized simultaneously.

Co-localization of two dye-conjugated antibodies against different parts of the same fusion protein is sometimes not sufficient for the required FRET energy transfer. A complete antibody is a large Y-shaped protein molecule, ~150 kDa in size, made up of two heavy chains and light chains. Owing to the length of an antibody molecule (300 to 400 Ångstrom) and the flexibility of the hinge region, juxtaposed antibody molecules can bridge a relatively large distance.[15] Whereas closely juxtaposed FRET probes are in general sufficient for obtaining a FRET signal, it may be advantageous to stabilize and/or enhance juxtaposing two probes in order to increase FRET efficiency. For example, the size of a probe or a dye might interfere with FRET analysis via negative steric effects. Also, the flexibility of an antibody may decrease the probability of FRET occurrence between a pair of FRET dyes that are conjugated to antibody probes. When preparing a dye conjugate, like a fluorescent probe, it is in general not possible to control the site of conjugation. For example, in case of antibody conjugation, a dye moiety might become attached to different parts of the antibody molecule. Depending on the site of dye-conjugation, the spatial orientation of dyes on probes can be favorable or unfavorable for FRET energy transfer efficiency i.e. dyes attached to probes need not necessarily be within energy transfer distance of each other.

Surprisingly, the invention provides the insight that juxtaposing a set of probes can be modulated in order to increase the probability of FRET energy transfer between a pair of dyes, by providing at least one probe with a reactive group. The invention provides a set of at least a first and a second molecular probe, each probe provided with a dye wherein the dyes together allow energy transfer; at least one probe comprising a reactive group allowing juxtaposing at least first and second probe wherein the reactive group allows modulation of juxtaposing the probes such that there is an increased likelihood of energy transfer between the dyes. Use of such a probe set allows to detection of juxtaposed probes with an improved sensitivity compared to use of probes not comprising any reactive groups.

In the present context, the term "reactive group" refers to a moiety that allows modulating the spatial organization of FRET dyes such that there is an increase in the probability of energy transfer to occur and/or an increase in energy transfer efficiency. The spatial organization refers to both the distance between the dyes as well as to their relative orientation. Modulating the spatial organization includes adjusting and stabilizing the spatial organization of dyes. One of the primary conditions for energy transfer to occur is that donor and acceptor molecules must be in close proximity, typically 10-100 Å. In a preferred embodiment, a reactive group allows juxtaposing the dyes within a distance of 100 Å of each other, more preferably within 50 Å of each other but most preferably within a distance of 20 Å of each other. It is therefore preferred that a reactive group is small, e.g., smaller than 10 kiloDalton (kD), more preffered, smaller than 5 kDa, even more preffered, smaller than 2 kDa or most preffered, smaller than 1 kDa. For example, a reactive group is biotin.

As the, a reactive group allows modulating juxtaposed probes such that there is an increased likelihood of energy transfer between dyes by directly interacting with another probe. For example, a reactive group of a first probe binds to a part of a juxtaposed second probe to form a stable complex between the probes in a spatial orientation that is favorable for FRET to occur. As mentioned above with respect to the site of dye conjugation, it is often not possible to selectively modify a probe with a reactive group at a defined site. The site of modification is mainly determined by the presence and accessibility of a certain residue via which a reactive group is conjugated to a probe, e.g. via primary amines or via thiol groups. Thus, an antibody probe may contain a reactive group at either the constant and/or the variable region of the immunoglobulin. It is conceivable that not every site is equally suitable for interacting with a second probe e.g. due to steric hindrance. Therefore, it is preferred that a probe is provided with a multiplicity of reactive groups to statistically increase its capacity to interact with another probe. For example, a probe is provided with two or three or even five reactive groups.

Provided herein is a method for detecting the presence of a fusion protein in a cell using a set of at least a first and a second molecular probe, each probe capable of recognizing a binding site (via its binding domain) positioned at opposite sides of the fusion region of the fusion protein, each probe further provided with a dye wherein the dyes together allow energy transfer, at least one probe provided with a reactive group allowing modulation of juxtaposing the at least first and the second probe such that there is an increased likelihood of energy transfer between the dyes, comprising providing a set of probes, providing a sample comprising a cell, contacting the sample with the probes under conditions that allow juxtaposing the probes on the fusion protein, removing any unbound and any non-specifically bound probe and detecting juxtaposition of the probes via FRET to determine the presence of the fusion protein. In case a first probe can interact directly with at least a second probe, it is preferred to contact the sample with each probe in consecutive steps with extensive intermittent washing procedures to avoid self association between probes. For example, a sample is contacted with probe A, comprising a reactive group, to allow recognition of and binding to one part of a fusion protein. Next, any unbound and any non-specifically bound probe A is removed by repeated washing steps. Subsequently, the sample is contacted with probe B reactive with another part of the fusion protein under conditions allowing juxtaposing probe A and B on the same fusion protein. Also here, any unbound and any non-specifically bound probe B is preferably removed by repeated washing steps. In one embodiment of the invention, a reactive group of probe A interacts with at least a juxtaposed probe B to enhance and/or stabilize the spatial orientation of the dyes present on the probes such that there is an increased likelihood of energy transfer between them. Although this method can be used to detect the presence of a fusion protein, it shall be clear that such a procedure, involving multiple separate contacting and washing steps, can be rather laborious and time-consuming. Moreover, if probes are capable of directly interacting with each other, a significant background staining can be expected caused by probes binding to the subdomains on the normal proteins that are derived from the normal genes instead of the fusion gene. In the example above, a reactive group of probe A which is bound to the native protein A might recruit and interact with probe B. Also, if not all unbound probe A is efficiently removed, an unwanted interaction between probe A and B can occur upon contacting the sample with probe B. Both events may result in a detectable energy transfer signal, despite the fact that probe B is not juxtaposed to probe A on a fusion protein.

Thus, in a preferred embodiment of the invention, a reactive group of a first probe is not directly or immediately reactive with a second probe in order to avoid self association of the probes. This is advantageous for an optimal recognition of a fusion protein by each probe and for juxtaposing the probes on the fusion protein. Moreover, it avoids untimely energy transfer to occur between directly connected or multimerized probes and decreases an aspecific background signal. This is important to ensure that an energy transfer signal truly reflects juxtaposed probes.

The invention provides the insight that, if a reactive group of a first probe is not reactive with at least a second probe in order to avoid self association of the probes, a so-called "bridging" substance may be used to mediate an interaction between the probes, allowing to modulate juxtaposing the probes such that there is an increased likelihood of energy transfer between the dyes on the probes. A substance may be any kind of compound capable of binding to or modifying a probe, a reactive group and/or a dye to modulate the spatial organization of dyes on juxtaposed probes such that it is favorable for FRET. Preferably, a substance allows juxtaposing the dyes within a distance of 2 to 100 Ångstrom of each other. The substance is preferably added to a sample following binding of dye-conjugated probes to a target fusion protein, in an amount effective to modulate the spatial organization of the dyes on juxtaposed probes. Advantageously, the substance binds to a reactive group with a high specificity and a high affinity. Also, it is preferred that such a substance is relatively small so that the bridging substance only minimally affects the distance between a pair of dyes and the relative orientation of a pair of dyes.

In a preferred embodiment, a method is provided for detecting the presence of a fusion protein in a cell using a set of at least a first and a second molecular probe, each probe capable of recognizing a binding site positioned at opposite sides of the fusion region of the fusion protein, each probe further provided with a dye wherein the dyes together allow energy transfer, at least one probe provided with a reactive group allowing to modulate juxtaposing at least first and the second probe such that there is an increased likelihood of energy transfer between the dyes, wherein a reactive group of the first probe is not directly reactive with the second probe, comprising providing a set of probes providing a sample comprising a cell, contacting the sample with the probes, under conditions that allow juxtaposing the probes on the fusion protein, removing any unbound and any non-specifically bound probe, contacting the probes with a substance capable of linking at least a reactive group of the first probe to the second probe and detecting juxtaposition of the probes via FRET to determine the presence of the fusion protein.

A method using a probe set at least one probe comprising a reactive group wherein probes do not directly interact and require a bridging substance has several advantages. First, an improved specificity and reduced background staining can be achieved compared to a method using probes which can directly interact. After all, for a reactive group to exert its effect via a bridging substance, probes need to be in a close juxtaposition of each other prior to the addition of the substance i.e. resulting from binding of one probe adjacent to another probe on the same fusion protein. Second, the procedure is fast and easy because no separate contacting/washing steps are required for each individual probe. Thus, it permits to contact a sample with a mixture of probes all together in a single action. Likewise, any unbound and any non-specifically bound probes can be removed simultaneously. Much preferred, as exemplified herein in the detailed description, is a set of at least a first and a second molecular probe, each probe provided with a dye wherein the dyes together allow energy transfer; each probe provided with a reactive group. A substance is preferably capable of binding, or "bridging", at east two reactive groups. In a preferred embodiment, each probe within a set of probes is provided with the same reactive group. Also, each probe within a set of probes may be provided with a different reactive group but having the same reactivity. This allows the use of one type of bridging substance having at least two identical binding sites for a reactive group.

In a preferred embodiment, a probe is provided with more than one reactive group, enabling the probe to interact with more than one molecule of bridging substance. Providing a probe with more than one reactive group will theoretically increase the likelihood of an interaction between the probe and a bridging substance. Furthermore, for the ease of practicing the present invention, a suitable reactive group or a derivative thereof is commercially available and can be easily and efficiently attached to a probe.

In accordance with the present invention, a particularly interesting reactive group is biotin, with avidin or streptavidin being a particularly suitable bridging substance. Avidin is an egg-white derived glycoprotein with a molecular weight of about 68000 daltons and a diameter of 8 to 10 Ångstrom. It consists of four identical subunit chains. One avidin or streptavidin molecule can bind four molecules of biotin. Avidin has an extraordinarily high affinity(affinity constant $>10^{15}$ M−1) for biotin. This high affinity assures the user of a rapidly formed and stable complex between avidin and the biotin-labeled probes. The protein streptavidin, produced by the bacterium *Streptomyces avidinii*, has a structure very similar to avidin, and also binds biotin tightly. It often exhibits lower non-specific binding, and thus is frequently used in place of avidin. Once a biotin-avidin complex forms, the bond is essentially irreversible. The biotin-avidin system is widely used and has proven to be very useful in the detection and localization of antigens, glycoconjugates, and nucleic acids by employing biotinylated antibodies, lectins, or nucleic acid probes. As the, a reactive group with such a small size is advantageous for achieving a close distance between a dye pair. Biotin is a vitamin with a molecular weight of only 244 daltons. Also, many biotin molecules can be coupled to a protein, enabling the biotinylated protein to bind more than one molecule of avidin. Avidin, streptavidin and biotin are available from many commercial sources. Various standard procedures for preparing biotin-conjugates are known to those skilled in the art, most of which can be completed within a day. Moreover, commercial biotinylation kits are available that contain all the necessary components for protein biotinylation.

If a set of probes is used wherein each probe is provided with a different reactive group, a suitable substance comprises a molecule capable of binding at least one of each reactive group. Alternatively, such a binding substance comprises a complex of at least two molecules that can be covalently or non-covalently attached to each other, wherein each molecule is capable of binding to a reactive group.

The invention provides a method for detecting a fusion protein at the single cell level using of a set of probes according to the invention, each probe capable of binding to a binding site positioned at opposite sides of a fusion region of the fusion protein via the binding domain of the probe i.e. one probe is directed against a protein fragment comprising the N-terminal fragment of a fusion protein, and an other probe is directed against a protein fragment comprising the C-terminal fragment of the same fusion protein. A fusion protein comprises any kind of proteinaceous substance which is formed after transcription and translation of a fusion gene. A fusion gene comprises one part of one or more genes combined with another gene or a part derived thereof. A fusion protein may be the result of a chromosomal translocation, inversion or deletion. In a preferred embodiment, a method provided is used to detect a tumor-specific fusion protein. A fusion protein may be an endogenously expressed protein or it may be the result of genetic engineering. Fusion proteins in malignancies which can readily be detected using a method according to the invention include but are not limited to those listed in Table I.

It is of great relevance to note that the present method does not require disruption of the cell integrity, e.g. the preparation of a cell lysate, to detect the presence of an intracellular fusion protein. Preservation of the morphology integrity of a cell permits analysis at the single cell level, for example by flow cytometry or fluorescence microscopy. Detection of a FRET signal by flow cytometry offers the ability to perform rapid, multiparametric analysis of specific individual cells in a heterogeneous population. The main advantage of flow cytometry is that it directly gives quantitative data and that it is very rapid (results can be obtained in a few hours).

The method provided in the present invention allows detection of a fusion protein at the single cell level. In a preferred embodiment, the method provided is used to detect an intracellular protein at the single cell level. When detecting an intracellular fusion protein, a sample comprising a cell is treated so as to obtain a permeabilization of the material and a preservation of the morphology. The preferred treatment is one which fixes and preserves the morphological integrity of the cellular matrix and of the proteins within the cell as well as enables the most efficient degree of probe, e.g. antibody, penetration.

Unlike for example a "catching/detection" antibody method, which can essentially only be applied to detect the presence of a fusion protein at the cell surface or in a cell lysate, the present method allows gating of subset of cells that are present in a mixture of cells via immunophenotypic characteristics. Consequently, the method provided herein permits the detection of a fusion protein in a rare population of malignant cells in a large background of normal cells. This is especially advantageous for detecting low frequencies of fusion-positive cells like in the case of detection of minimal residual disease (MRD) during or after treatment for evaluation of treatment effectiveness. In preferred embodiment, the method provided includes multiparameter flow cytometry to identify and/or isolate single cells to detect the presence of a fusion protein at the single cell level. All that is required for practicing the method provided is a flow cytometry facility. Importantly, the procedure can be performed in routine laboratories by personnel with ordinary skills.

More than a hundred different fusion genes and fusion proteins have been described in various types of cancer. As the, the method provided allows to discriminate between the presence of normal proteins and an aberrant fusion protein at the single cell level. Theoretically, two antibodies recognizing two different domains of a fusion protein can cause a background staining by binding to the domains on the normal proteins that are derived from the normal genes instead of the fusion gene. However, generally only one of the two normal proteins reaches a detectable expression level in a target cell population, as defined by cell surface and/or intracellular markers. Furthermore, the normal proteins and the fusion protein often differ in their intracellular expression pattern, frequently resulting in a different subcellular localization.[16,17] This implies that coincidental co-localization of the two different normal proteins is unlikely to occur at a significant level in the target cell population. In particular, coincidental juxtaposing probes sufficient for a FRET signal will be rare in normal cells, if this occurs at all.

Provided herein is a method for producing a set of at least a first and a second molecular probe, each probe provided with a dye wherein the dyes together allow energy transfer; at least one probe provided with a reactive group allowing juxtaposing the first and second probe, comprising contacting each probe with a dye to form a conjugate between the probe and the dye and purifying the conjugate, further comprising contacting at least one probe with reactive group or a derivative thereof to form a conjugate between the probe and the reactive group and purifying the conjugate. The Förster radius ($R_0$) is the distance corresponding to 50% energy transfer efficiency and it characterizes each donor/acceptor pair. Its value is generally between 30 and 60 Ångstrom. In the present context, the term "dye" refers to a substituent that, in concert with another dye, can be used for energy transfer analysis, such as FRET analysis. As mentioned above, FRET is usually based on the interaction between donor and acceptor dyes that are both fluorescent. In one embodiment, the invention uses a set of probes wherein at least one of the dyes is a fluorochrome. However, a nonfluorescent acceptor may also be used and FRET is detected by quenching of donor fluorescence. As said, detecting FRET by monitoring a decrease in donor fluorescence as a consequence of juxtapositioned probes is often not as sensitive as detecting in increase in acceptor fluorescence. Thus, in a preferred embodiment, at least two fluorescently labeled probes are used to detect a fusion protein, as is exemplified in the detailed description. Examples of preferred fluorochromes are those suitable for analysis by conventional flow cytometry and include fluorescein labels, e.g. 5-(and 6-) carboxyfluorescein, 5- or 6- carboxyfluorescein, 6-(fluorescein)-5-(and 6-) carboxamide hexanoic acid and fluorescein isothiocyanate, Alexa Fluor dyes such as Alexa Fluor 488 or Alexa Fluor 594, cyanine dyes such as Cy2, Cy3, Cy5, Cy7, optionally substituted coumarin, R-phycoerythrin, allophycoerythrin, Texas Red and Princeton Red as well as conjugates of R-phycoerythrin and, e.g. Cy5 or Texas Red and members of the phycobiliproteins. Other dyes of interest are quantum dot dyes, which come in a nearly unlimited palette of colors. Extensive information on donor/acceptor pairs suitable for energy transfer detection by flow cytometry can be found in Szollosi et al.[18] Preferred combinations of fluorochromes comprise those dyes used in the classical tandem conjugates, also referred to as duochromes.[19]

The method provided comprises providing a sample comprising a cell, whereby the sample is optionally subject to fixation and permeabilization if an intracellular fusion protein is to be detected. A sample may comprise a primary cell that is obtained from a biological sample. A biological sample can be a body fluid sample including blood, serum, urine, bone marrow, cerebrospinal fluid (CSF), or saliva. It may also be a tissue sample or tissue homogenate. A sample comprises a cultured cell that may be a cultured primary cell, for example, tumor cells obtained from a lymph node biopsy. Furthermore, a sample may comprise a cultured cell from an established laboratory cell line, like a K562, KASUMI-1, REH or CEM cell line, which can be obtained from a number of sources such as the American Type Culture Collection (ATCC; worldwideweb:atcc.org for an online catalog. The method provided is suitable for detection of the presence of an endogenous fusion protein, as well as a recombinant fusion protein, in a cell.

For analyzing a sample comprising a suspension of cells, it is preferred that the sample is treated so as to obtain a preservation of the morphology of the material and permeabilization in order to ensure sufficient accessibility of a molecule of interest to a probe. The type of treatment will depend on several factors, for instance on the fixative used, the extent of fixation and the type and properties of the molecule of interest. Fixation may be carried out with a fixative such as formaldehyde.

For the detection of a fusion protein in primary cells, it is especially advantageous to use an additional marker to define a target cell population of interest. A number of important biological applications in infectious diseases, MRD detection and monitoring, and gene therapy typically require the analysis and isolation of rare cells (e.g. haemopoietic stem/progenitor cells) from a large background. In one embodiment of the invention, the method includes staining a sample for at least one cellular marker, like a cell surface marker or an intracellular marker, to define a target cell population within a mixture of cells comprising contacting the sample with a compound capable of selectively binding to the marker. In a preferred embodiment, such a compound is directly tagged with a fluorescent dye. A suitable compound comprises a fluorescently labeled antibody or a binding fragment functionally equivalent thereto. Also, a compound capable of selectively binding to a cellular marker can be used which can be detected using a dye-conjugated secondary reagent (e.g. a fluorescently labeled secondary antibody). A cellular marker comprises any kind of intracellular or membrane-bound marker which can be used to distinguish a subpopulation of cells in a mixture of cells. A mixture of cells comprises living cells. It also comprises permeabilized and/or fixed cells. A cellular marker can be a cluster of differentiation (CD) antigen. CD markers are cell surface molecules of, among others, haemopoietic cells that are distinguishable with monoclonal antibodies. Haemopoietic cells comprise thymocytes, dendritic cells, Langerhans' cells, neutrophils, eosinophils, germinal centre B cells, follicular dendritic cells, plasma cells and bone-marrow cells. For example, suitable cellular markers comprise CD1, CD3, CD4, CD8, CD10, CD19, CD20, CD33, CD34 and CD117. Monoclonal antibodies directed against a large number of human CD markers can be obtained from various suppliers, such as BD Biosciences or Ancell Immunology search Products, Bayport, USA. Often, antibodies are available that are directly conjugated with a fluorochrome of choice e.g. CD10-PE or CD19-FITC, which is obviously a preferred choice to practice a method according to the invention.

In a preferred embodiment, a method is provided to identify and/or isolate rare single cells using multiparameter flow cytometry/cell sorting techniques and to further characterize these cells by the presence or absence of a fusion protein of interest. Such a method is particularly suited for application to a number of important problems in immune system development, infectious diseases, cancer and gene therapy. Typically, prior to staining a cell sample with a probe set, cells are labeled with at least one relevant dye-conjugated antibody according to standard procedures in order to define a target cell population. The choice of dye should preferably, but not exclusively, aim at the usage of two or three dyes for immunophenotyping in addition to the FRET dyes for detection of a fusion protein. For example, a FRET probe set according to the invention can be combined with another dye to mediate leukocyte subset gating via immunophenotypic characteristics, e.g. CD10, CD19 and CD20 to accurately define subsets of precursor-B-cells in bone marrow, or CD1, CD4 and CD8 to define subsets of thymocytes, or CD84 and/or CD117 to identify stem/precursor cell populations. As shown herein in the detailed description, the invention provides a method that allows the detection of an intracellular fusion protein in a very small subset of cells, i.e. detection of MRD, which is essential for evaluating effectiveness of cancer treatment.

The invention provides a diagnostic test kit for detecting the presence of a fusion protein in a cell comprising a set of probes according to the invention For example, such a kit may be used for monitoring and quantification of malignant cells, e.g. leukemic cells, via the detection of tumor-specific fusion protein-positive cells. The diagnostic test kit provided herein is useful at the time of diagnosis as well as during and after treatment to evaluate the effectiveness of the applied cancer treatment protocol.

TABLE I

Examples of fusion proteins in malignacies that can be detected via antibody-mediated FRET technology.

| Malignancy | Chromosome aberration | Fusion prrotein |
|---|---|---|
| Precurso-B-ALL | t(1;19)(q23;p13) | E2A-PBX1 |
|  | t(4;11)(q21;q23) | MLL-AF4 |
|  | t(9;22)(q34;q11) | BCR-ABL |
|  | t(12;21)(p13;q22) | TEL-AML1 |
| Acute myeloid leukemia | t(8;21)(q22;q22) | AML1-ETO |
|  | t(15;17)(q22;q21) | PML-RARA |
|  | inv(16)(p13;q22) | CBFB-MYH11 |
| Lymphoma | t(2;5)(p23;q35) | NPM-ALK |
| Ewing sarcoma | t(11;12)(q24;q12) | EWS-FLI1 |

DETAILED DESCRIPTION OF THE INVENTION

Figure 1:
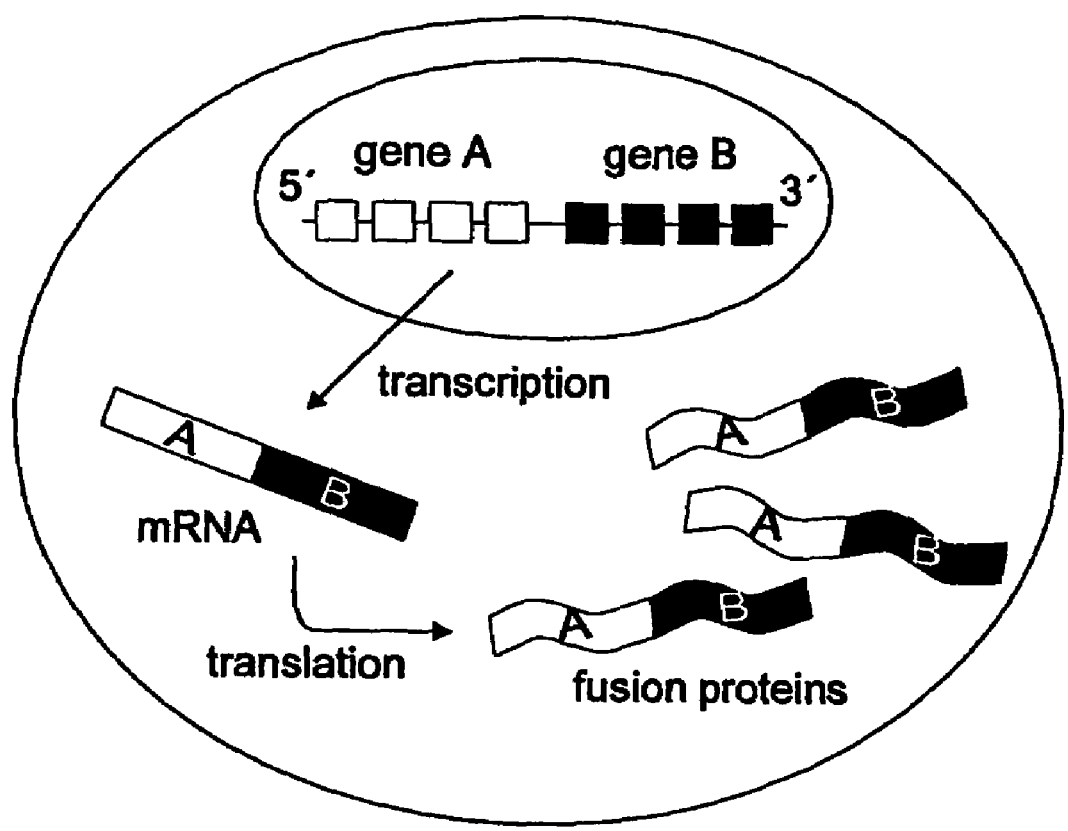
FIG. 1. Schematic diagram of a fusion gene consisting of the upstream (5') part of gene A and the downstream (3') part of gene B. This A-B fusion gene is transcribed into A-B mRNA and translated into a A-B fusion protein.
Figure 2:
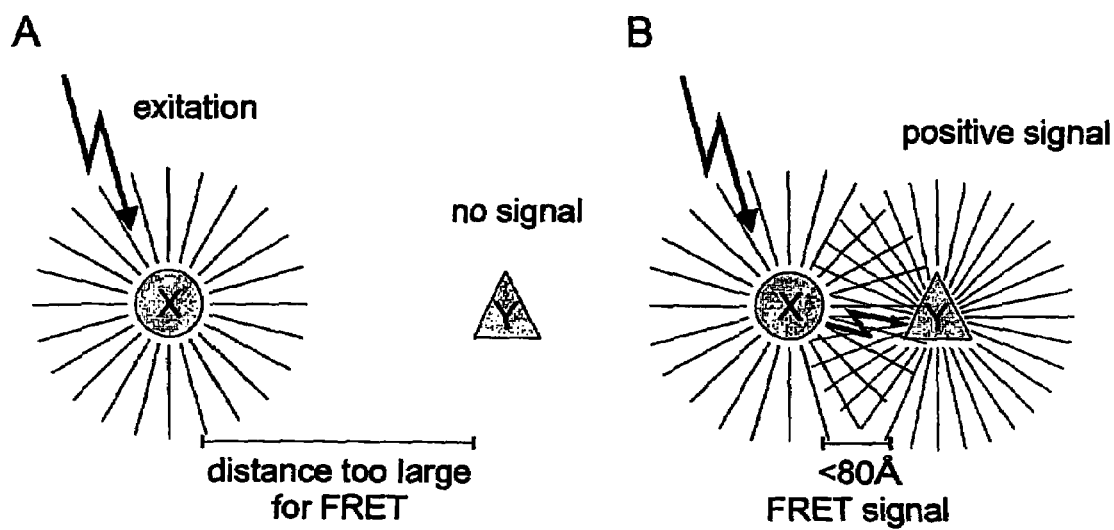
FIG. 2. Schematic diagram of the principle of fluorescence resonance energy transfer (FRET) with fluorochrome X as donor dye and Y as acceptor dye. A. The acceptor dye Y will not be excited by the emission light of the donor dye X, if the distance between X and Y is too large. B. If the distance between the donor and acceptor dye is sufficiently small (<80 Angstrom but preferably<50 Angstrom), the emission light of the donor dye X will excite the acceptor dye Y.
Figure 3:
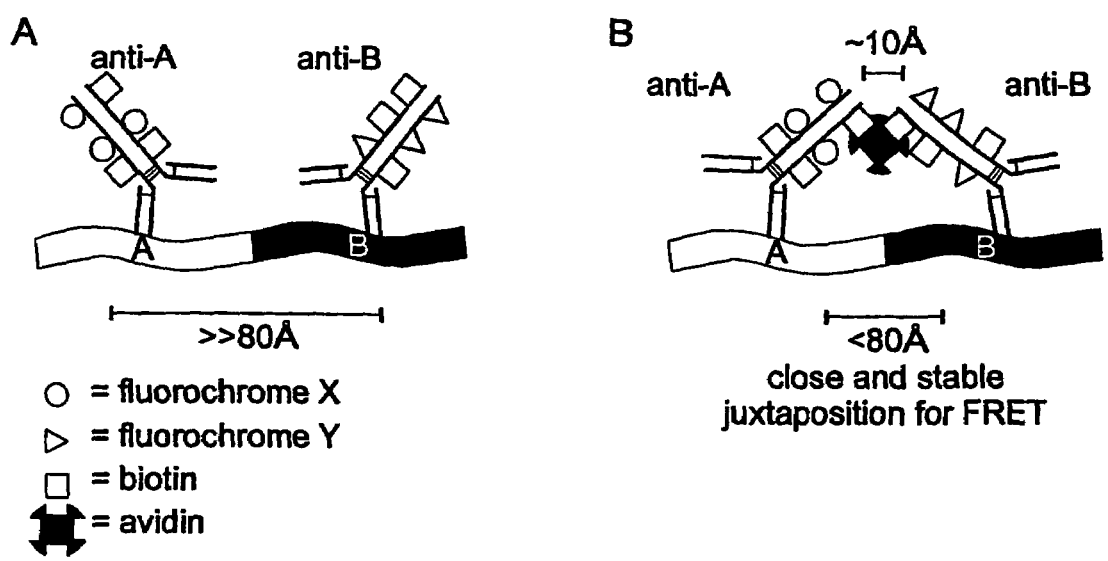
FIG. 3. Schematic diagram of the A-B fusion protein recognized by a set of anti-A and an anti-B antibody probes. A. Probe A is conjugated with donor dye X and probe B is conjugated with acceptor dye Y (see FIG. 2). Furthermore, both probes are conjugated with biotin as a reactive group. B. After incubation with antibody probes A and B, the probes can be bound together via incubation with avidin, provided that the two probes indeed recognize and bind to the same A-B fusion protein. This juxtaposition of the two antibodies (stabilized by the biotin-avidin system) is detectable via the FRET principle (see FIG. 2).

As mentioned above, the present invention relates to a method for determining the presence of a fusion protein in a cell using a probe set. This method can be used to diagnose various types of cancer which involve chromosomal translocations, inversions or deletions that give rise to a fusion gene. For example, approximately 35% of adult patients with acute lymphoblastic leukemia (ALL) and chronic myeloid leukemia (CML) are associated with a specific chromosomal defect, a translocation between chromosomes 9 and 22 that creates the Philadelphia (Ph) chromosome. This translocation occurs at the site in the genome of a protein tyrosine kinase named ABL, creating the abnormal BCR-ABL fusion protein, a gene product of the in-frame fusion of the ABL gene with another gene called BCR. Generally, fusion proteins play an important role in the oncogenetic process. For example, the kinase activity of ABK in the BCR-ABL fusion protein is activated and deregulated, driving the uncontrolled cell growth observed in ALL and in CML. When acute lymphoblastic leukemia is diagnosed in a patient, typically comprising traditional cytogenetics such as karyotype analysis for the Ph chromosome, the total number of leukemia cells is approximated to $10^{11}$ to $10^{13}$. A majority of patients reach complete remission after about 5 weeks of chemotherapy. Complete remission does not mean that the leukemic cells are totally eradicated from the body but that their level is beyond the sensitivity level of classical cytomorphologic methods (e.g. 1 to 5%). At this time, up to $10^{10}$ malignant cells can still remain in the patient. They represent the minimal residual disease (MRD). Detection of low frequencies of residual malignant cells allows a longer follow-up of the tumor burden during chemotherapy and thus, permits to better appreciate the sensitivity of leukemia cells to treatment. It is now established that the level of MRD represents a powerful prognostic factor for final outcome. Besides, the detection of an increase of the MRD level enables to anticipate impending relapse. The method provided in the present invention allows to discriminate between the presence of normal proteins and an aberrant fusion protein at the single cell level.

As an example of this method we will describe the preparation of a probe set for the detection of the TEL-AML1 fusion protein. Also described is a method using this probe set to detect the presence of TEL-AML1 fusion protein in ALL cells at the time of diagnosis and during follow-up to detect the level of MRD.

EXAMPLE

Preparation of a Set of Probes

Preferably, a probe set according to the invention comprises a set of two fluorochrome-conjugated antibodies each antibody additionally provided with a reactive group. Methods of producing an antibody are known to those skilled in the art. For example, to obtain a polyclonal antibody, a laboratory animal is immunized with an immunogen such as a recombinant protein or a synthetic peptide. The animal's immune response is monitored by taking test bleeds and determining the titer of the reactivity. When appropriately high titers are obtained, blood is collected from the animal and antisera are prepared.

Further fractionation of the antisera to enrich for antibodies reactive to the protein can be done if desired. See e.g. Harlow et al. *Antibodies. A Laboratory Manual*, Cold Spring Harbor Publications, New York (1988). Monoclonal antibodies can be obtained by various techniques known in the art, for example by fusing spleen cells of immunized mice with a myeloma cell line by the addition of polyethylene glycol (PEG). Fused cells are cultured in a selection medium, e.g. medium containing a mixture of hypoxanthine, aminopterin and thymidine. Fused cells that survive in this selection medium are tested for the production of the desired antibody (often by solid-phase immunoassay such as ELISA) and, if positive, the cultures are cloned so that there is only one cell in each culture well. This produces a clone of cells from a single progenitor which is both immortal and a producer of monoclonal antibody. Antibodies obtained can be characterized using conventional immunodiagnostic techniques e.g., by Western blotting using lysates of cells expressing a recombinant fusion protein or by ELISA.

Biotinylation of Antibodies

Biotin is typically conjugated to proteins via primary amines (i.e., lysines). Usually, between three and six biotin molecules are conjugated to each antibody. Dialyze or exchange over a column the antibody in 100 mM carbonate, pH 8.4. Measure the antibody concentration after buffer equilibration. (For IgG, 1 mg/ml has an $A_{280}$ of 1.4). If the antibody concentration is less than 1 mg/ml, the conjugation will probably be sub-optimal. If necessary, dilute the antibody to a concentration of 4 mg/ml. Dissolve 10 mgs of biotin (N-hydroxysuccinimidobiotin, Pierce) in 1 ml anhydrous DMSO (anhydrous dimethyl sulfoxide, Aldrich) immediately before use. The reactive biotin molecule is unstable. Once the biotin is solubilized, it should be used immediately. Add biotin to give a ratio of 80 μg per mg of antibody; mix immediately. Wrap the tube in foil; incubate and rotate at room temperature for two hours. Remove the unreacted biotin and exchange the antibody into 10 mM Tris pH 8.2, 150 mM NaCl, pHix (5 mg/ml pentachlorophenol in 95% ethanol (use as 10,000×, or 3-4 drops per liter) Sigma).

FITC Conjugation of an Antibody

FITC is a small organic molecule, and is typically conjugated to proteins via primary amines (i.e., lysines) of an immunoglobulin. Usually, between three and six FITC molecules are conjugated to each antibody; higher conjugations can result in solubility problems as well as internal quenching (and reduced brightness). Thus, an antibody will usually be conjugated in several parallel reactions to different amounts of FITC, and the resulting reagents will be compared for brightness (and background stickiness) to choose the optimal conjugation ratio. The entire conjugation can be performed in about a half-day. The reactive fluorescein molecule, fluorescein isothiocyanate, is unstable. Once a vial has been cracked and the FITC solubilized, it should be used immediately. Since single vials of FITC contain sufficient material for ~100 mgs of antibody, it is economical to perform multiple FITC conjugations on the same day.

1. Antibody Preparation

Dialyze or exchange over a column the antibody in 500 mM carbonate, pH 9.5. Measure the antibody concentration after buffer equilibration. (For IgG, 1 mg/ml has an $A_{280}$ of 1.4). If the antibody concentration is less than 1 mg/mL, the conjugation will probably be sub-optimal. If necessary, dilute the antibody to a concentration of 4 mg/ml.

2. Covalent Conjugation

Dissolve 10 mgs (the entire contents of 1 vial; no need to weigh) of FITC (Molecular Probes) in anhydrous DMSO immediately before use. Add FITC to give a ratio of 40-80 µg per mg of antibody; mix immediately. Wrap the tube in foil; incubate and rotate at room temperature for one hour. Remove the unreacted FITC and exchange the antibody into 500 mM carbonate, pH 9.5 by gel filtration or dialysis.

3. Characterization of the Conjugate

Determine F/P and protein concentration by measuring the absorbance at 280 and 495 nm. IgG: 1 mg/ml has an A(280) of 1.4; mw=150,000. IgM: 1 mg/ml has an A(280) of 1.2; mw=900,000. Fluorescein: 1 mM has an A(495) of 68 and an A(280) of 11.8. F/P values of 3-10 are probably optimal for any particular IgG.

Protein concentration:
IgG (mg/ml)=[A(280)−0.31*A(495)]/1.4
IgM (mg/ml)=[A(280)−0.31*A(495)]/1.2
F/P ratio:
IgG: 3.1*A(495)/[A(280)−0.31*A(495)]
IgM: 15.9*A(495)/[A(280)−0.31*A(495)]

Detection by FRET Analysis

Figure 4:
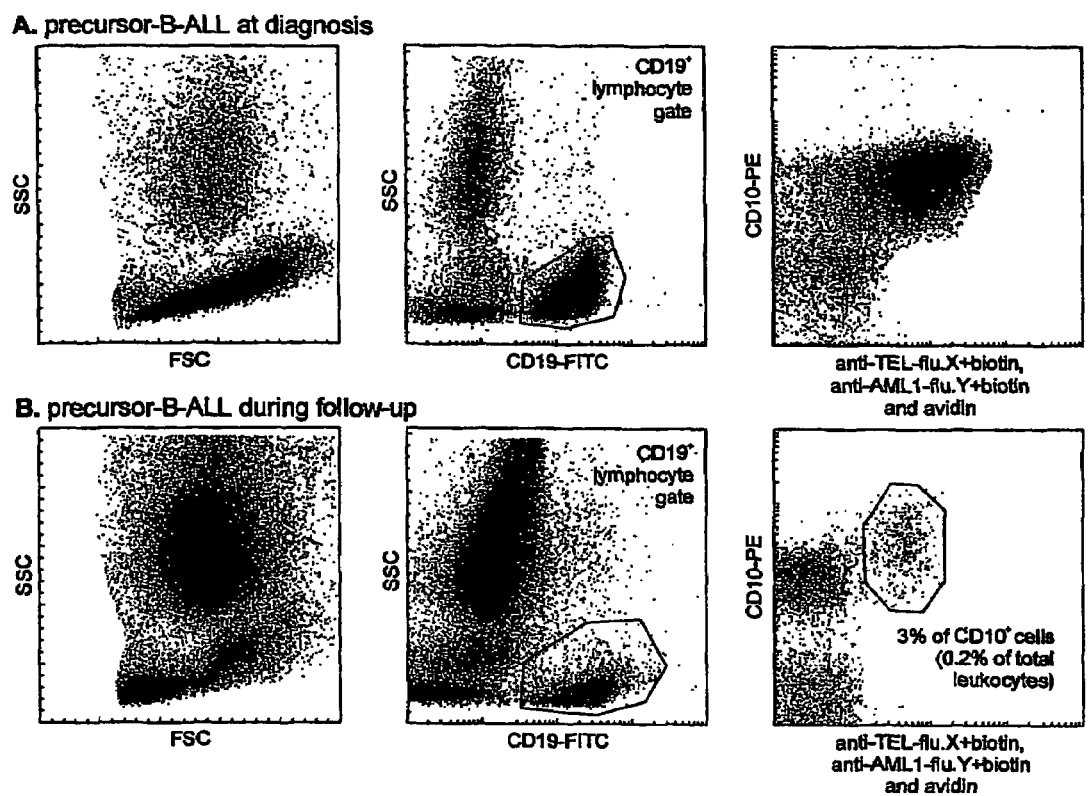
FIG. 4. Example of FRET-mediated detection of the TEL-AML1 fusion protein in ALL cells. A. Precursor B-ALL cells at diagnosis. Flow cytometric gating on ALL blast cells as defined by light scatter characteristics (left), followed by gating on CD 19+ blast cells (middle), and evaluation of the presence of the TEL-AML1 fusion protein within the CD10$^+$/CD19$^+$ ALL cells (right). B. Precursor B-ALL cells during follow-up. Flow cytometric detection of low frequencies of TEL-AML1 positive cells (minimal residual disease) during follow-up for evaluation of treatment effectiveness. Only 3% of the CD10+ blasts was positive for TEL-AML1 fusion protein, i.e. only 0.2% of total leukocytes.

A bone marrow sample is obtained from an ALL patient and leukocytes are isolated according to standard procedures. Leukocytes are labeled with two cell surface markers to define a leukocyte subset via immunophenotypic characteristics. FITC-conjugated monoclonal anti-human CD19 (FITC-CD19) and PE-conjugated monoclonal anti-human CD10 (PE-CD10) were used. Cells are then fixed according to standard procedures, e.g. in 1% paraformaldehyde, to preserve the integrity of the cell and its content. The cell membrane is permeabilized using a detergent such as saponin to make the cell interior accessible to probe set. Cells are labeled for one hour at 4° C. in the dark with a mixture containing a probe set according to the invention (0.1 to 0.3 microgram/ml of each probe), comprising a Cy3-labeled biotin-conjugated antibody against the helix-loop-helix motif of TEL and a Cy5-labeled biotin-conjugated antibody against the Runt domain of AML1. After washing of the cells to remove unbound probe, the cells are incubated with unlabeled avidin to induce sufficiently close and stable juxtaposing of the two different antibodies. The cells are then analyzed in a flow cytometer. Results are shown in FIG. 4. Panel A shows the evaluation of the TEL-AML1 fusion protein in precursor-B-ALL cells obtained from a patient at the time of diagnosis. ALL blast cells are first gated on the basis of their light scatter characteristics (forward scatter versus side scatter). Then, CD 19-positive blast cells are gated (FL1 versus side scatter). The presence of the TEL-AML1 fusion protein is readily detectable in the subset of CD19+/CD10+ ALL cells. In panel B, similar analyses are shown from the same patient after a five week therapy protocol to evaluate the effectiveness of the treatment. Only 3% of the CD10+ blast cells is positive for the TEL-AML1 fusion protein, i.e. only 0.2% of total leukocytes. The detection of such a low frequency of TEL-AML1-positive cells (minimal residual disease) has not been shown before.

We have used the FaesCalibur to perform FRET measurements using Cy3 and Cy5 as donor/acceptor pair. The 488 nm excitation is not optimal for Cy3 (543 would be better), 632 is optimal for Cy5, and with this setup we could obtain reasonable good FRET distribution curves (actually they are better than that obtained with FITC/TRITC pair because the autofluorescence is much less of a problem). In addition we could use the 488->520 band for autofluorescence correction on a cell-by-cell basis. Data acquisition and analysis were performed using Cell Quest Pro software.

REFERENCES

1. Jaffe E. S., N. L. Harris, H. Stein and J. W. Vardimaij (eds), World Health Organization classification of tumors. Pathology and genetics of tumors of hematopoietic and lymphoid tissues. Lyon: IARC Press, 2001.
2. Van Dongen J. J. M., E. A. Macintyre, J. A. Gabert, et al., Standardized RT-PCR analysis of fusion gene transcripts from chromosome aberrations in acute leukemia for detection of minimal residual disease. Report of the BIOMED-1 Concerted Action: investigation of minimal residual disease in acute leukemia. Leukemia 1999; 13:1901-28.
3. T. H. Rabbitts, Chromosomal translocations in human cancer. Nature 1994; 372: 143-9.
4. Look A. T., Oncogenic transcription factors in the human acute leukemias. Science 1997; 278:1059-64.
5. Crans H. N., and K. M. Sakamoto, Transcription factors and translocations in lymphoid and myeloid leukemia. Leukemia 2001; 15:313-31.
6. Van Denderen J., A. Hermans, T. Meeuwsen, et al., Antibody recognition of the tumor-specific bcr-abl joining region in chronic myeloid leukemia. J. Exp. Med. 1989; 169:87-98.
7. Van Denderen J., P. ten Hacken, P. Berendes, et al., Antibody recognition of the tumor-specific b3-a2 junction of bcr-abl chimeric proteins in Philadelphia-chromosome-positive leukemias. Leukemia 1992; 6: 1107-12.
8. Sang B. C., L. Shi, P. Dias, et al., Monoclonal antibodies specific to the acute lymphoblastic leukemia t(1;19)-associated E2A/PBX1 chimeric protein: characterization and diagnostic utility. Blood 1997; 89:2909-14.
9. Berendes P., Recognition of tumor-specific proteins in human cancer, Ph.D. Thesis, Chapter 8. Rotterdam: Erasmus University Rotterdam, 1997: 111-27.
10. Worldwideweb: probes.com/handbook/tables/1570.html 11. Matyus L., Fluorescence resonance energy transfer measurements on cell surfaces. A spectroscopic tool for determining protein interactions. J. Photochem. Photobiol. B. 1992; 12:323b-37.
12. Broudy V. C., N. L. Lin, H. J. Buhring, et al., Analysis of c-kit receptor dimerization by fluorescence resonance energy transfer. Blood 1998; 91:898-906.
13. Chan F. K., R. M. Siegel, D. Zacharias, et al., Fluorescence resonance energy transfer analysis of cell surface receptor interactions and signaling using spectral variants of the green fluorescent protein. Cytometry 2001; 44:361-8.
14. Van den Beemd R., P. P. Boor, van Lochem, W. C. Hop, A. W., Langerak, I. L. M. Wolvers-Tettero, H. Hooijkaas, J. J. M. van Dongen. Flow cytometric analysis of the Vbeta repertoire in healthy controls. Cytometry 2000; 40:336-345.
15. I. Roitt. *Essential Immunology*. Oxford: Blackwell Scientific Publications; 2001; 37-58.
16. Falini B., L. Flenghi, M. Fagioli, et al., Immunocytochemical diagnosis of acute promyelocytic leukemia (M3) with the monoclonal antibody PG-M3 (anti-PML). Blood 1997; 90:4046-53.
17. Falini B., D. Y. Mason Proteins encoded by genes involved in chromosomal alterations in lymphoma and leukemia: clinical value of their detection by immunocytochemistry. Blood 2002; 99:409-26.
18. Szollosi J., S. Damjanovich, L. Matyus, Application of fluorescence resonance energy transfer in the clinical laboratory: Routine and research. Cytometry 1998; 34:159-179.
19. Tanke, H. J. Fluorochromen voor twee- en drievoudige labelingen. *Immunofenotypering in de diagnostiek: indicatiestellingen, uitvoering en interpretatie. Eds. Van Dongen, Groeneveld, Adriaansen, Hooijkaas* (ISBN 90-73436-16-8). 1994; pages 55-61.

What is claimed is:

1. A method for detecting a fusion protein's presence in a cell using a set of molecular probes comprising at least a first and a second molecular probe, each molecular probe able to recognize a binding site positioned at opposite sides of the fusion protein's fusion region, each molecular probe further directly conjugated to a dye wherein said dyes together allow energy transfer, the first and the second molecular probes directly conjugated to a reactive group that modulates the molecular probes' spatial organization after binding to a molecule of interest such that an increased likelihood of energy transfer exists between said dyes, wherein a reactive group of said first molecular probe is not involved in binding to the molecule of interest and not directly reactive with said second molecular probe, said method comprising:
 providing the set of molecular probes,
 providing a sample comprising a cell,
 contacting said sample with said set of probes under conditions that allow binding of said molecular probes directly to any such fusion protein within said sample,
 contacting said molecular probes with a substance comprising at least two identical binding sites for the reactive group and able to link at least a reactive group of said first molecular probe to at least a reactive group of said second molecular probe, and
 detecting juxtaposition of said molecular probes via fluorescence resonance energy transfer (FRET) to determine any such fusion protein's presence.

2. The method according to claim 1 wherein said substance causes said dyes to come within a distance of 2 to 100 Ångstrom of each other.

3. The method according to claim 1 wherein said reactive group comprises biotin and wherein said substance comprises avidin or streptavidin.

* * * * *